US012471911B2

(12) United States Patent
Munday

(10) Patent No.: US 12,471,911 B2
(45) **Date of Patent: *Nov. 18, 2025**

(54) APPARATUS FOR CLOSING A SURGICAL SITE

(71) Applicant: George Swope Munday, Danville, KY (US)

(72) Inventor: George Swope Munday, Danville, KY (US)

(73) Assignee: George Swope Munday, Danville, KY (US)

( * ) Notice: Subject to any disclaimer, the term of this patent is extended or adjusted under 35 U.S.C. 154(b) by 203 days.

This patent is subject to a terminal disclaimer.

(21) Appl. No.: 18/305,832

(22) Filed: Apr. 24, 2023

(65) Prior Publication Data

US 2023/0263517 A1 Aug. 24, 2023

Related U.S. Application Data

(62) Division of application No. 17/571,992, filed on Jan. 10, 2022, now Pat. No. 11,701,104.

(51) Int. Cl.
*A61B 17/04* (2006.01)
*A61B 17/06* (2006.01)
*A61B 17/00* (2006.01)

(52) U.S. Cl.
CPC .... *A61B 17/0482* (2013.01); *A61B 17/06133* (2013.01); *A61B 17/06061* (2013.01)

(58) Field of Classification Search
CPC ................ A61B 17/0482; A61B 17/06; A61B 17/06061; A61B 17/06133; A61B 2017/00477
USPC ................................................ 606/144, 228
See application file for complete search history.

(56) References Cited

U.S. PATENT DOCUMENTS

| | | | |
|---|---|---|---|
| 633,404 | A | 9/1899 | Warburton |
| 3,901,244 | A | 8/1975 | Schweizer |
| 4,582,196 | A | 4/1986 | Hughson |
| D301,373 | S | 5/1989 | Peters |
| 4,967,902 | A | 11/1990 | Sobel et al. |
| 5,021,059 | A | 6/1991 | Kensey et al. |

(Continued)

FOREIGN PATENT DOCUMENTS

| | | | |
|---|---|---|---|
| CN | 206482618 | U | 9/2017 |
| CN | 107811664 | A | 3/2018 |

(Continued)

OTHER PUBLICATIONS

PCT Search Report and Written Opinion completed by the ISA/US and issued in connection with PCT/US2018/045517.

(Continued)

*Primary Examiner* — Anthony D Stashick
*Assistant Examiner* — Marcos Javier Rodriguez Molina
(74) *Attorney, Agent, or Firm* — Barnes & Thornburg LLP

(57) ABSTRACT

A suturing device includes a clamshell body having a first side coupled to a second side by a hinge at a hinge end. The first side and the second side each have a cantilevered end opposite the hinge end. The clamshell body is configured to actuate between an open position and a closed position. A suture retainer is positioned within the clamshell body and is configured to receive a suture. An opening is formed in a wall of the second side of the clamshell body.

20 Claims, 14 Drawing Sheets

(56) References Cited

U.S. PATENT DOCUMENTS

| | | | |
|---|---|---|---|
| 5,059,201 | A | 10/1991 | Asnis |
| 5,089,012 | A | 2/1992 | Prou |
| 5,099,994 | A | 3/1992 | Kalinski et al. |
| 5,160,339 | A | 11/1992 | Chen et al. |
| 5,171,253 | A | 12/1992 | Klieman |
| 5,179,818 | A | 1/1993 | Kalinski et al. |
| 5,325,868 | A | 7/1994 | Kimmelstiel |
| 5,413,585 | A | 5/1995 | Pagedas |
| 5,507,775 | A | 4/1996 | Ger et al. |
| 5,514,159 | A | 5/1996 | Matula et al. |
| 5,675,961 | A | 10/1997 | Cerwin et al. |
| 5,683,402 | A | 11/1997 | Cosgrove et al. |
| 5,735,877 | A | 4/1998 | Pagedas |
| 5,830,157 | A | 11/1998 | Foote |
| 5,911,728 | A | 6/1999 | Sepetka et al. |
| 5,944,739 | A | 8/1999 | Zlock et al. |
| 6,015,428 | A | 1/2000 | Pagedas |
| 6,050,981 | A | 4/2000 | Lampropoulos et al. |
| 6,066,160 | A | 5/2000 | Colvin et al. |
| 6,126,677 | A | 10/2000 | Ganaja et al. |
| 6,143,004 | A | 11/2000 | Davis et al. |
| 6,200,329 | B1 | 3/2001 | Fung et al. |
| 6,214,332 | B1 | 4/2001 | Askill et al. |
| 6,293,961 | B2 | 9/2001 | Schwartz et al. |
| 6,471,715 | B1 | 10/2002 | Weiss |
| 6,860,895 | B1 | 3/2005 | Akerfeldt et al. |
| 6,939,357 | B2 | 9/2005 | Navarro et al. |
| 6,986,780 | B2 | 1/2006 | Rudnick et al. |
| 7,033,379 | B2 | 4/2006 | Peterson |
| 7,144,412 | B2 | 12/2006 | Wolf et al. |
| 7,204,841 | B2 | 4/2007 | Green |
| 7,351,249 | B2 | 4/2008 | Hnojewyj et al. |
| 7,407,505 | B2 | 8/2008 | Sauer et al. |
| 7,468,068 | B2 | 12/2008 | Kolster |
| 7,470,256 | B2 | 12/2008 | Lampropoulos et al. |
| 7,520,869 | B2 | 4/2009 | Lampropoulos et al. |
| 7,544,187 | B2 | 6/2009 | Lampropoulos et al. |
| 7,547,296 | B2 | 6/2009 | Lampropoulos et al. |
| 7,582,105 | B2 | 9/2009 | Kolster |
| 8,418,851 | B2 | 4/2013 | Culligan et al. |
| 9,220,489 | B2 | 12/2015 | Tegels |
| 9,326,765 | B2 | 5/2016 | Lane et al. |
| 9,370,368 | B2 | 6/2016 | Jayant |
| 9,468,435 | B2 | 10/2016 | Ashland |
| 9,636,105 | B2 | 5/2017 | Bagaoisan et al. |
| 9,655,622 | B2 | 5/2017 | Jonn et al. |
| 9,775,601 | B2 | 10/2017 | Keating et al. |
| 10,660,635 | B2 | 5/2020 | Munday |
| 11,701,104 | B2 * | 7/2023 | Munday ............. A61B 17/0482 606/144 |
| 2003/0204195 | A1 | 10/2003 | Keane et al. |
| 2004/0133239 | A1 | 7/2004 | Singhatat |
| 2004/0177594 | A1 * | 9/2004 | Dey ................. A61B 17/06133 53/118 |
| 2004/0260344 | A1 | 12/2004 | Lyons et al. |
| 2005/0033365 | A1 | 2/2005 | Courage |
| 2005/0085855 | A1 | 4/2005 | Forsberg |
| 2006/0058844 | A1 | 3/2006 | White et al. |
| 2006/0069397 | A1 | 3/2006 | Nobles et al. |
| 2006/0106418 | A1 | 5/2006 | Seibold et al. |
| 2006/0106423 | A1 | 5/2006 | Weisel et al. |
| 2006/0265006 | A1 | 11/2006 | White et al. |
| 2007/0004991 | A1 | 1/2007 | Shelton |
| 2007/0032821 | A1 | 2/2007 | Chin-Chen et al. |
| 2007/0210131 | A1 | 9/2007 | Yarborough et al. |
| 2008/0015635 | A1 | 1/2008 | Olsen et al. |
| 2008/0015636 | A1 | 1/2008 | Olsen et al. |
| 2008/0017526 | A1 * | 1/2008 | Prescott ........... A61B 17/06133 206/63.3 |
| 2008/0097479 | A1 | 4/2008 | Boehlke et al. |
| 2008/0269785 | A1 | 10/2008 | Lampropoulos et al. |
| 2008/0300629 | A1 | 12/2008 | Surti |
| 2009/0043246 | A1 | 2/2009 | Dominguez |
| 2009/0069847 | A1 | 3/2009 | Hashiba et al. |
| 2009/0076546 | A1 | 3/2009 | Ashley et al. |
| 2009/0143817 | A1 | 6/2009 | Akerfeldt |
| 2009/0234295 | A1 | 9/2009 | Lampropoulos et al. |
| 2009/0275980 | A1 | 11/2009 | Zeiner et al. |
| 2010/0230300 | A1 | 9/2010 | Hunter et al. |
| 2011/0046667 | A1 | 2/2011 | Culligan et al. |
| 2011/0215005 | A1 | 9/2011 | Cerwin et al. |
| 2012/0010634 | A1 | 1/2012 | Crabb et al. |
| 2013/0165954 | A1 | 6/2013 | Dreyfuss et al. |
| 2013/0310856 | A1 | 11/2013 | Sherts et al. |
| 2015/0038991 | A1 | 2/2015 | Prior et al. |
| 2015/0088195 | A1 | 3/2015 | Moustafa |
| 2015/0157316 | A1 | 6/2015 | Labarbera |
| 2016/0376240 | A1 | 12/2016 | Bunnelle et al. |
| 2017/0112487 | A1 | 4/2017 | Martin et al. |
| 2017/0245846 | A1 | 8/2017 | Kim |
| 2017/0245852 | A1 | 8/2017 | Kim |
| 2023/0414910 | A1 | 12/2023 | Culligan et al. |

FOREIGN PATENT DOCUMENTS

| | | | | | |
|---|---|---|---|---|---|
| DE | 19904281 | A1 | * | 10/1999 | ............. B65B 43/60 |
| EP | 0460784 | A1 | | 12/1991 | |
| EP | 494081 | B1 | | 1/1992 | |
| EP | 0494081 | A1 | | 7/1992 | |
| EP | 0608138 | A2 | | 7/1994 | |
| EP | 608138 | A3 | | 3/1995 | |
| EP | 0760227 | A1 | * | 3/1997 | ....... A61B 17/06133 |
| EP | 2363079 | A1 | * | 9/2010 | ......... A61B 17/0469 |
| JP | H0852143 | A | * | 2/1996 | ............. B65B 63/06 |
| JP | 2013-534170 | A | | 9/2013 | |
| JP | 2015-231572 | A | | 12/2015 | |
| KR | 101736309 | B1 | | 5/2017 | |
| WO | 9826719 | A1 | | 6/1998 | |
| WO | 0051498 | A1 | | 9/2000 | |
| WO | 2006050080 | A2 | | 5/2006 | |
| WO | 2008033766 | A2 | | 3/2008 | |
| WO | 2008150773 | A1 | | 12/2008 | |
| WO | 2009052509 | A1 | | 4/2009 | |
| WO | 2009114811 | A2 | | 9/2009 | |
| WO | WO-2011112433 | A1 | * | 9/2011 | ............. A61B 17/04 |
| WO | WO-2015138966 | A1 | * | 9/2015 | .......... A61B 17/0483 |
| WO | WO-2016014579 | A1 | * | 1/2016 | ....... A61B 17/06133 |
| WO | WO-2016175935 | A1 | * | 11/2016 | ....... A61B 17/06133 |
| WO | 2017180092 | A1 | | 10/2017 | |

OTHER PUBLICATIONS

Japanese Office Action for Application No. 2021-514281, dated May 12, 2022, 4 pages.

Extended European Search Report for Application No. 22162407.5, dated Aug. 29, 2022, 85 pages.

* cited by examiner

APPARATUS FOR CLOSING A SURGICAL SITE

CROSS-REFERENCE TO RELATED APPLICATIONS

This application is divisional application of U.S. patent application Ser. No. 17/571,992, filed Jan. 10, 2022, which is a continuation-in-part application of U.S. patent application Ser. No. 17/341,497, filed on Jun. 8, 2021, both of which are hereby incorporated by reference in their entirety.

TECHNICAL FIELD

The present disclosure relates to surgical instruments and particularly, to an instrument and method to enhance suture management within robotic surgical cases.

BACKGROUND

The use of robotic technology within the operating room has been increasing at an astounding rate. In 2017, there were approximately 644,000 robotic assisted surgical cases performed in the United States alone. Robotic assisted surgery is utilized globally in multiple surgical subspecialties. These include: cardiac surgery, thoracic surgery, gynecology, urology, otolaryngology, colorectal surgery, and general surgery. Within each of these specialties there are a variety of robotic cases in which suture is required.

Suture management within a robotic case is a common barrier to efficient surgical workflow. Poor suture management results in: increased operative times; knotting, fracturing, or accidental cutting of the suture; frustration for the surgeon; and ultimately a barrier to more frequent use of the robotic technology. Currently, surgeons navigate this suture management issue by substituting a long suture length with multiple shorter suture length to complete a case. This methodology generates increased total volume and expense of suture; increased OR expenses via longer operative times; and increased potential for a retained needle within the patient.

The disclosed embodiments will aid in efficient suture management in robotic surgery. It will decrease overall cost and increase patient safety across all robotic surgical specialties. Ultimately, this device and method will assist with the global proliferation of computer-aided surgery.

SUMMARY

The present disclosure includes one or more of the features recited in the appended claims and/or the following features which, alone or in any combination, may comprise patentable subject matter.

According to a first aspect of the disclosed embodiments, a suturing device includes a clamshell body configured to be inserted into a surgical site of a patient. The clamshell body has a first side coupled to a second side by a hinge at a hinge end. The first side and the second side each have a cantilevered end opposite the hinge end. The clamshell body is configured to actuate between an open position and a closed position. A suture retainer is positioned within the clamshell body and is configured to receive a suture. An is opening formed in a wall of the clamshell body. An end of the suture is configured to extend through the opening when the clamshell body is in the closed position so that the suture is accessible within the surgical site of the patient. A first side slot extends through the first side of the clamshell body. A cartridge is configured to be removably inserted through the first side slot. The suture is configured to be wound around the cartridge to assist in positioning the suture around the suture retainer.

In some embodiments of the first aspect, the suture retainer may extend from an inner wall of the first side of the clamshell body and may be positioned around the first side slot. The suture retainer may include a plurality of pegs arranged around the first side slot. The suture may be configured to be wound around the plurality of pegs. The cartridge may include a plurality of notches. Each of the plurality of pegs may be configured to rest within one of the plurality of notches when the cartridge is inserted through the first side slot.

Optionally, in the first aspect, a second side slot may extend through the second side of the clamshell body. At least a portion of the cartridge may extend through the second side slot when the cartridge is inserted through the first side slot and the clamshell body is moved to the closed position. When the cartridge is inserted through the first side slot, moving the clamshell body to the closed position may assist in positioning the suture around the suture retainer. When the cartridge is inserted through the first side slot and the clamshell body is moved to the closed position, the cartridge may be removable from the clamshell body through the first side slot. The cartridge may include a sloped end to enable the at least a portion of the cartridge to move through the second side slot when the clamshell body is moved to the closed position.

It may be desired, in the first aspect, that the suture may be configured to be positioned on the suture retainer at least one of during a medical procedure for the patient and before a medical procedure for the patient. At least one notch may be formed in at least one of the first side and the second side of the clamshell. A surgical robotic arm may be configured to couple to the clamshell body at the at least one notch.

According to a second aspect of the disclosed embodiments, a method of preparing a suturing device including a clamshell body configured to be inserted into a surgical site of a patient may include moving the clamshell body to an open position wherein a first side of the clamshell body is rotated away from a second side of the clamshell body. The first side is coupled to the second side by a hinge at a hinge end. The method also includes removably inserting a cartridge through a first side slot extending through the first side of the clamshell body. The method also include winding a suture around the cartridge to assist in positioning the suture around a suture retainer positioned within the clamshell body. The method also includes extending an end of the suture through an opening formed in a wall of the clamshell body. The method also includes moving the clamshell body to a closed position wherein the first side of the clamshell body is rotated toward the second side of the clamshell body. The end of the suture is configured to extend through the opening when the clamshell body is in the closed position so that the suture is accessible within the surgical site of the patient.

In some embodiments of the second aspect, the method may also include inserting the cartridge through the suture retainer when the cartridge is inserted into the first side slot. The suture retainer may include a plurality of pegs arranged around the first side slot. The method may also include inserting the cartridge between the plurality of pegs when the cartridge is inserted into the first side slot. The cartridge may include a plurality of notches. The method may also include positioning each of the plurality of pegs within one of the plurality of notches when the cartridge is inserted through the first side slot.

Optionally, in the second aspect, the method also includes extending at least a portion of the cartridge through a second side slot extending through the second side of the clamshell body when the cartridge is inserted through the first side slot and the clamshell body is moved to the closed position. The method may also include moving the clamshell body to the closed position to assist in positioning the suture around the suture retainer when the cartridge is inserted through the first side slot. The method may also include removing the cartridge from the clamshell body through the first side slot after the cartridge is inserted through the first side slot and the clamshell body is moved to the closed position. The cartridge may include a sloped end. The method may also include guiding the at least a portion of the cartridge to move through the second side slot with the sloped end when the clamshell body is moved to the closed position.

It may be contemplated, in the second aspect, that the method may also include positioning the suture on the suture retainer at least one of during a medical procedure for the patient and before a medical procedure for the patient. The method may also include coupling the clamshell body to a surgical robotic arm.

BRIEF DESCRIPTION OF THE DRAWINGS

The detailed description particularly refers to the accompanying figures in which.

DETAILED DESCRIPTION

Figure 1:
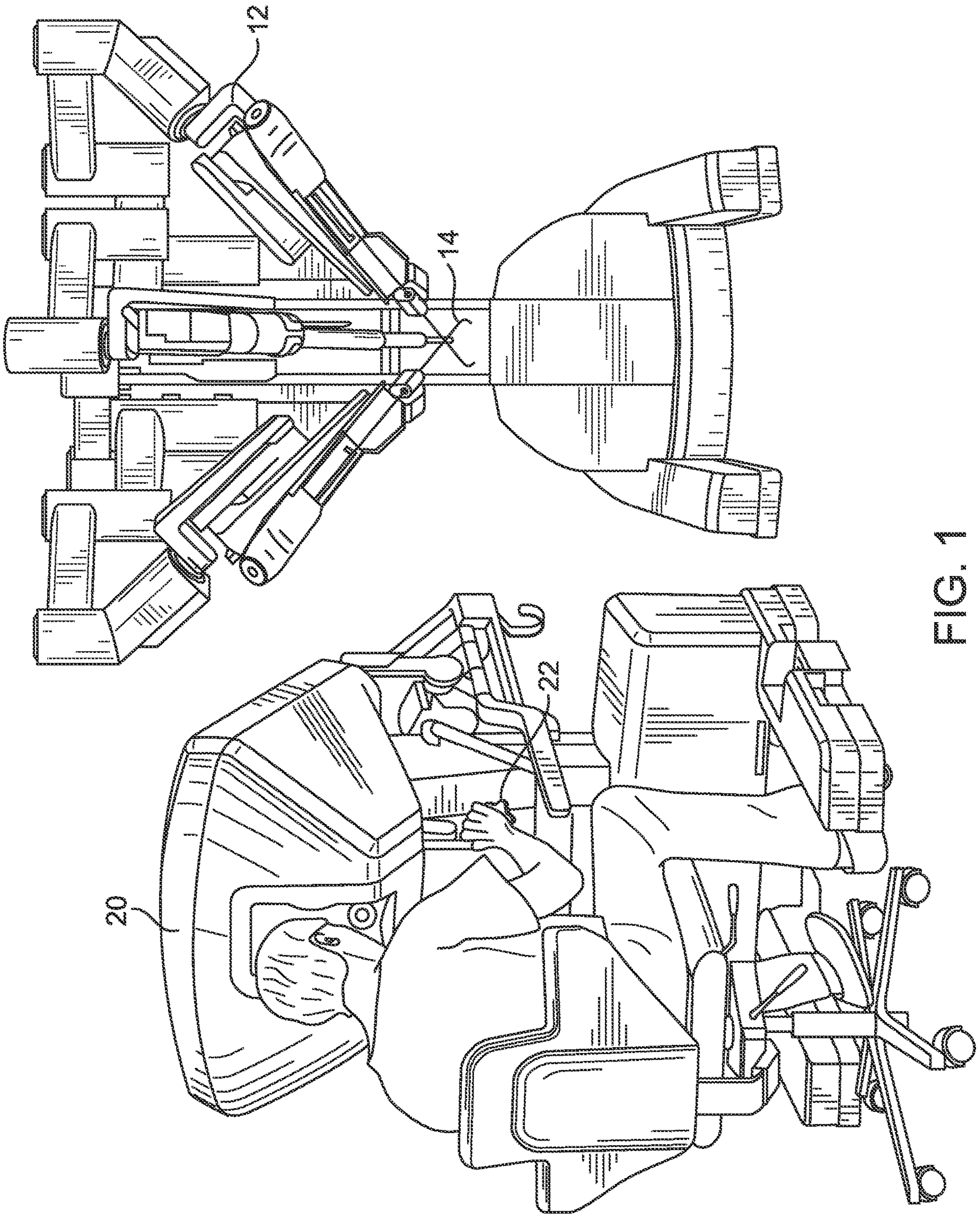
FIG. 1 is a perspective view of an automated surgical system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, an automated surgery system 10 includes at least one robotic arm 12 having a plurality of fingers 14 to grab surgical instruments. The robotic arm 12 is positioned at a surgical site so that the robotic arm 12 can manipulate the instruments at the surgical site. A control panel 20 includes a plurality of controls 22, e.g. a joystick, for a surgeon to manipulate the robotic arms 12 during surgery.

Figure 2:
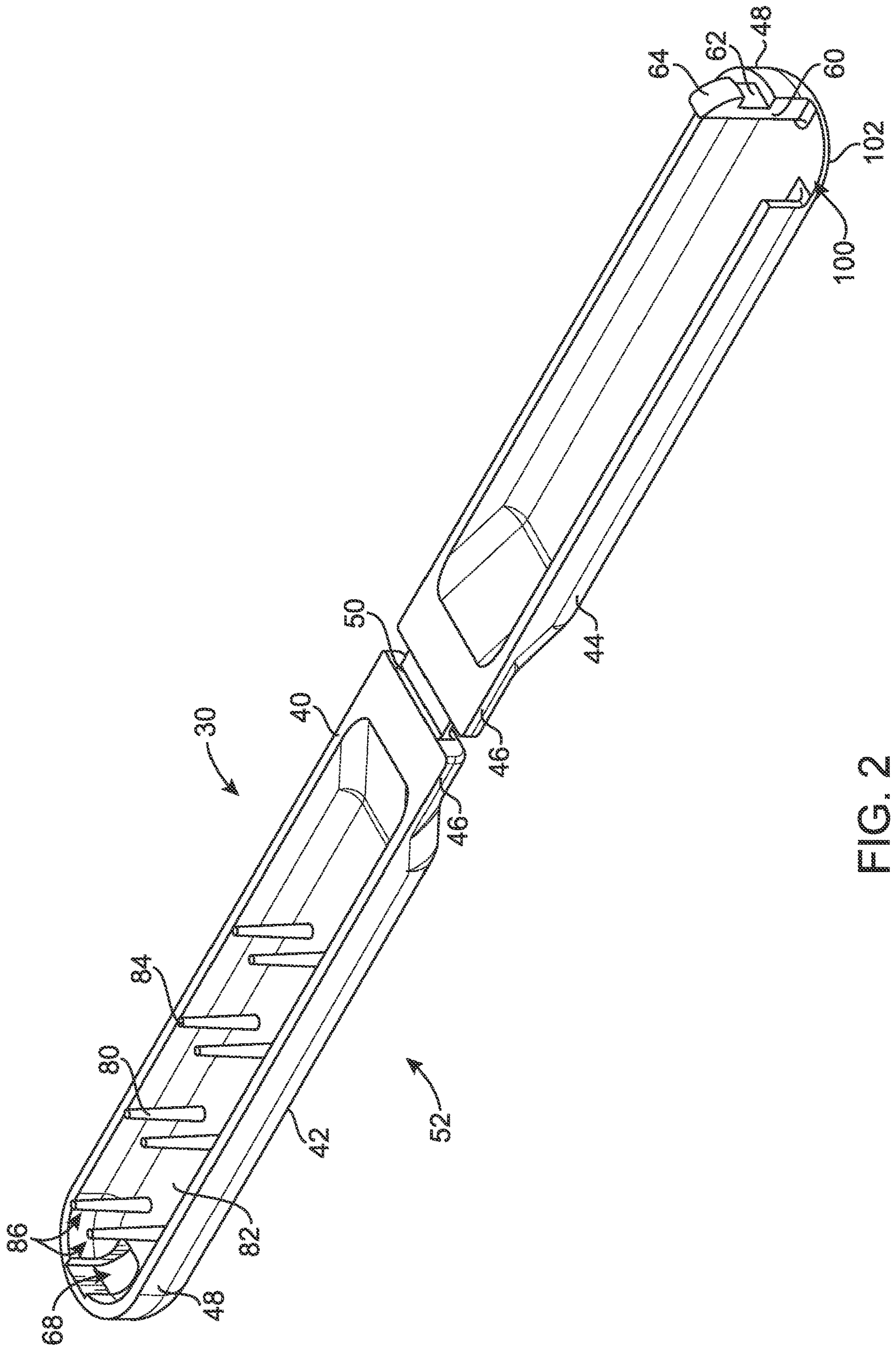
FIG. 2 is a top perspective view of a suturing device having a clamshell body including a first side coupled to a second side by a hinge at a hinge end, wherein the clamshell body is in an open position.

Referring to FIG. 2, a suturing device 30 is configured for use with the system 10 by securing the suturing device 30 to one of the plurality of fingers 14 of the robotic arm 12. The suturing device 30 is configured to be inserted into a surgical site of a patient to facilitate closing the surgical site after a surgical procedure. The suturing device 30 retains a suture 32 (described in more detail below) that can be pulled from the suturing device 30 to facilitate closing the surgical site. The suture 32 is configured to be pulled from the suturing device 30 while the suturing device 30 is inserted in the surgical site, e.g. inside the patient. The suture 32 is threaded through tissue that is to be closed before the suturing device 30 is removed from the surgical site. After the suturing device 30 is removed from the surgical site the suture 32 is tied together in at least one location to close the surgical site. In at least one embodiment, the suture 32 is wound within the suturing device 30 by a caregiver or technician prior to the surgical procedure. Accordingly, the suturing device 30 can accommodate any suture type used within a healthcare facility. A caregiver or technician selects the appropriate suture type for the surgical procedure, and the appropriate suture type is wound within the suturing device 30 at the healthcare facility prior to the surgical procedure. In another embodiment, the suturing device 30 may be pre-loaded with the suture 32.

Figure 4:
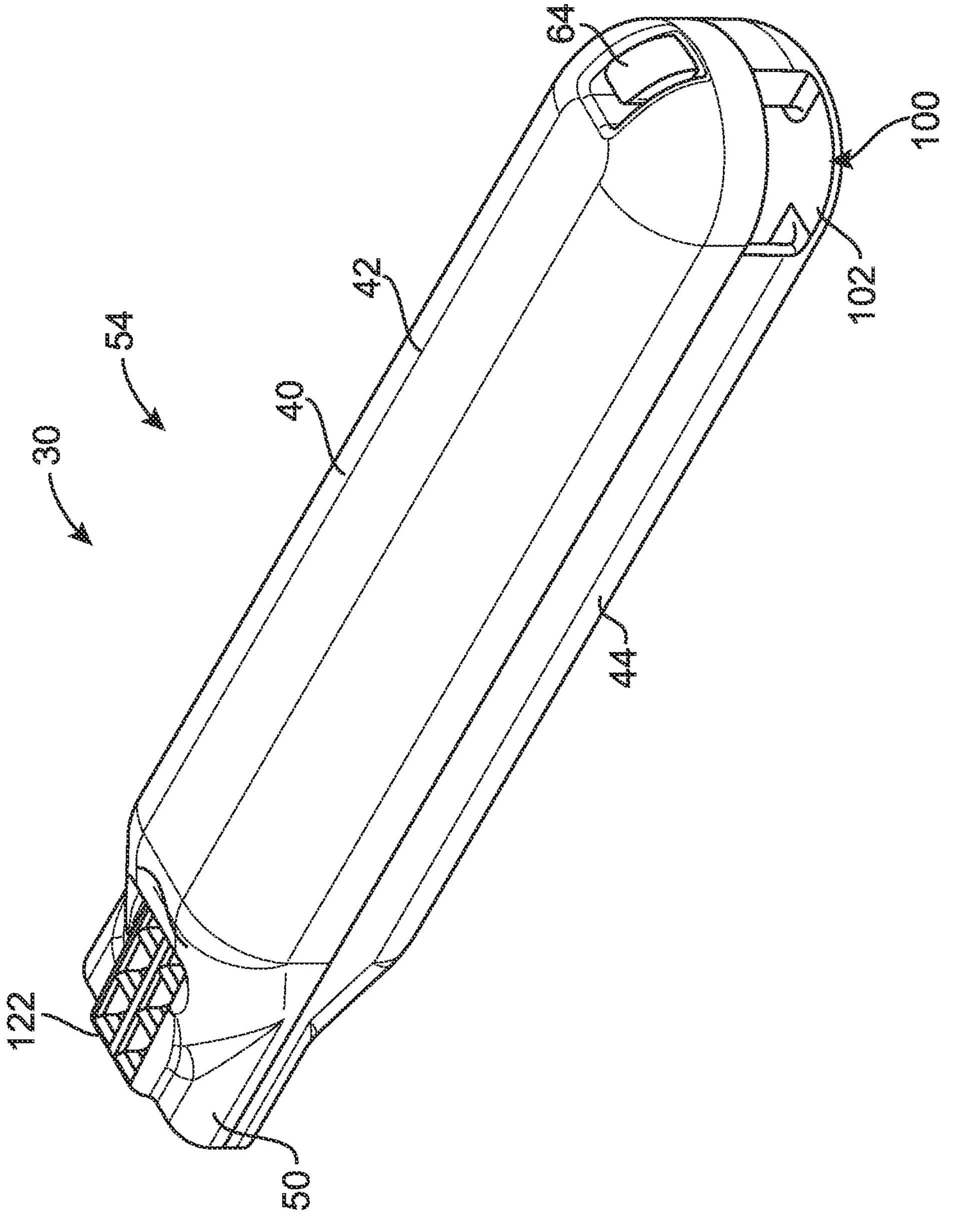
FIG. 4 is a top perspective view of the clamshell body in a closed position.

The suturing device 30 includes a clamshell body 40 having a first side 42 and a second side 44. Each of the first side 42 and the second side 44 includes a hinge end 46 and a cantilevered end 48. A pair of sidewalls 56 extend between the hinge end 46 and the cantilevered end 48 of each of the first side 42 and the second side 44. The first side 42 is coupled to the second side 44 by a hinge 50 at the hinge end 46 of the first side 42 and the second side 44. The hinge 50 enables the clamshell body 40 to articulate between an open position 52 (shown in FIG. 2) and a closed position 54 (shown in FIG. 4). The cantilevered end 48 of the second side 44 of the clamshell body 40 includes latch 60 having an arm 62 and an outwardly extending flange 64 extending from an end 66 of the arm 62. The cantilevered end 48 of the first side 42 of the clamshell body 40 includes an opening 68. The latch 60 is configured to extend though the opening 68 so that the flange 64 secures the first side 42 of the clamshell body 40 to the second side 44 of the clamshell body 40 when the clamshell body 40 is in the closed position 54 (as shown in FIG. 4).

Referring to FIG. 2, a suture retainer 80 is positioned within the clamshell body 40 and configured to receive the suture 32. The suture retainer 80 extends from an inner wall 82 of the first side 42 of the clamshell body 40. The suture retainer 80 includes a plurality of pegs 84 extending from the inner wall 82. In the illustrative embodiment, the plurality of pegs 84 are arranged in two rows 86 extending between the hinge end 46 and the cantilevered end 48 of the first side 42 of the clamshell body 40. In other embodiments, the suturing device 30 may include only one row 86 of pegs 84 or more than two rows 86 of pegs 84. It may be contemplated that the suturing device 30 only includes one peg 84 in some embodiments. In some embodiments, the caregiver or technician winds the suture 32 around the suture retainer 80 at the healthcare facility. In other embodiments, the suture is pre-loaded around the suture retainer 80.

An opening 100 is formed in the cantilevered end 48 of the second side 44 of the clamshell body 40. In the illustrative embodiment, the opening 100 is formed in a corner 102 of the cantilevered end 48 of the second side 44 of the clamshell body 40. In other embodiments, the opening 100 may be centered in the cantilevered end 48 of the second side 44 of the clamshell body 40. In yet another embodiment, the opening 100 may be formed in the sidewall 56 of the second side 44. It may also be contemplated that the opening 100 is formed in a sidewall 56 of the first side 42, in some embodiments. When the suture 32 is wound around the suture retainer 80, and end 110 of the suture 32 having a needle 112 extends from the suturing device 30 (as described in more detail below).

Figure 3:
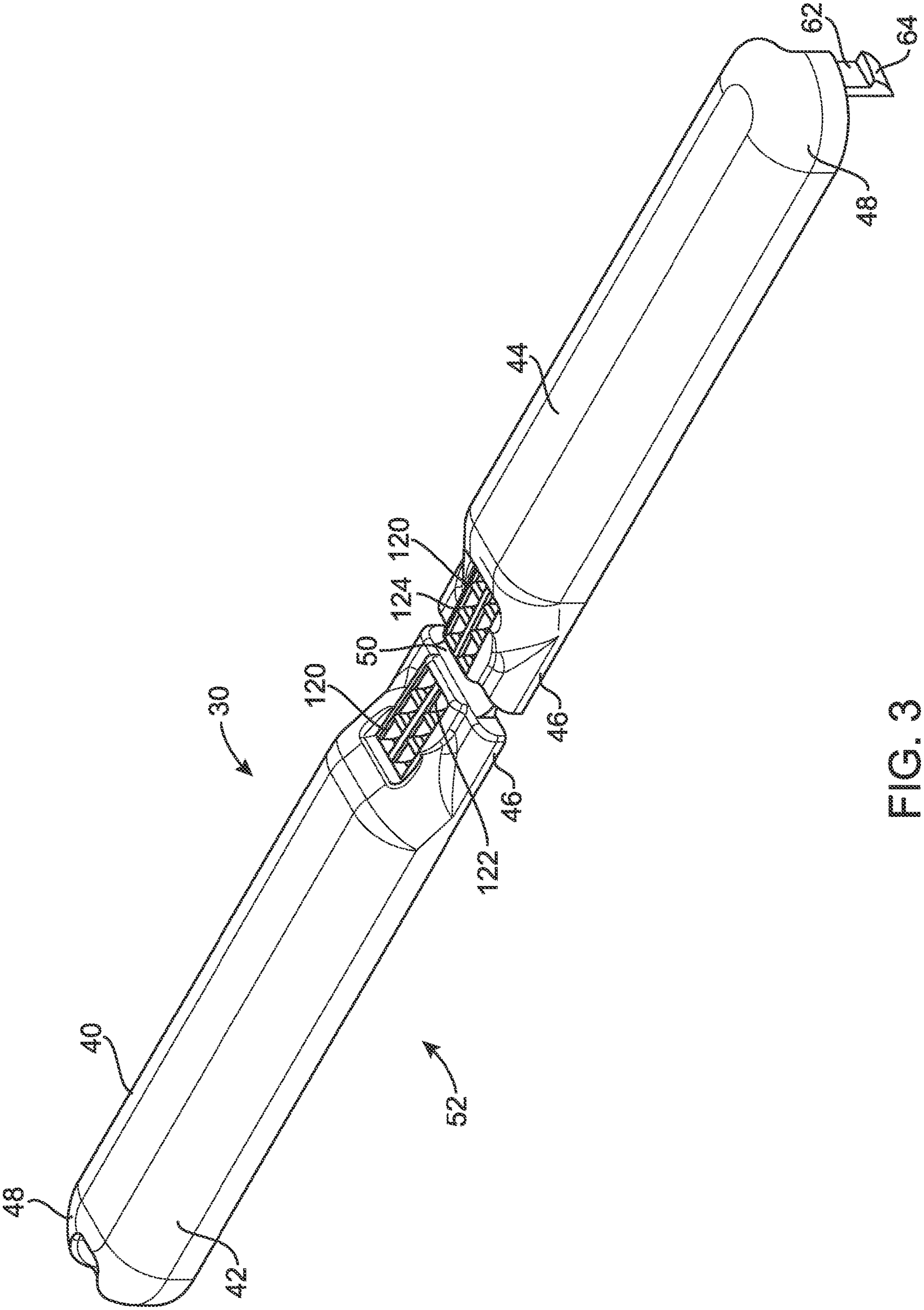
FIG. 3 is a bottom perspective view of the clamshell body in the open position.

Referring now to FIG. 3, notches 120 are formed adjacent the hinge end 46 of each of the first side 42 and the second side 44 of the suturing device 30. In particular, a first set of notches 122 are formed adjacent the hinge end 46 of the first side 42, and a second set of notches 124 are formed adjacent the hinge end 46 of the second side 44. In the closed position 54 (as shown in FIG. 4), the first set of notches 122 are positioned opposite the second set of notches 124. The fingers 14 of the robotic arm 12 are configured to grip the suturing device 30 at the notches 120 so that the suturing device 30 is secured to the system 10 during the surgical procedure.

Figure 5:
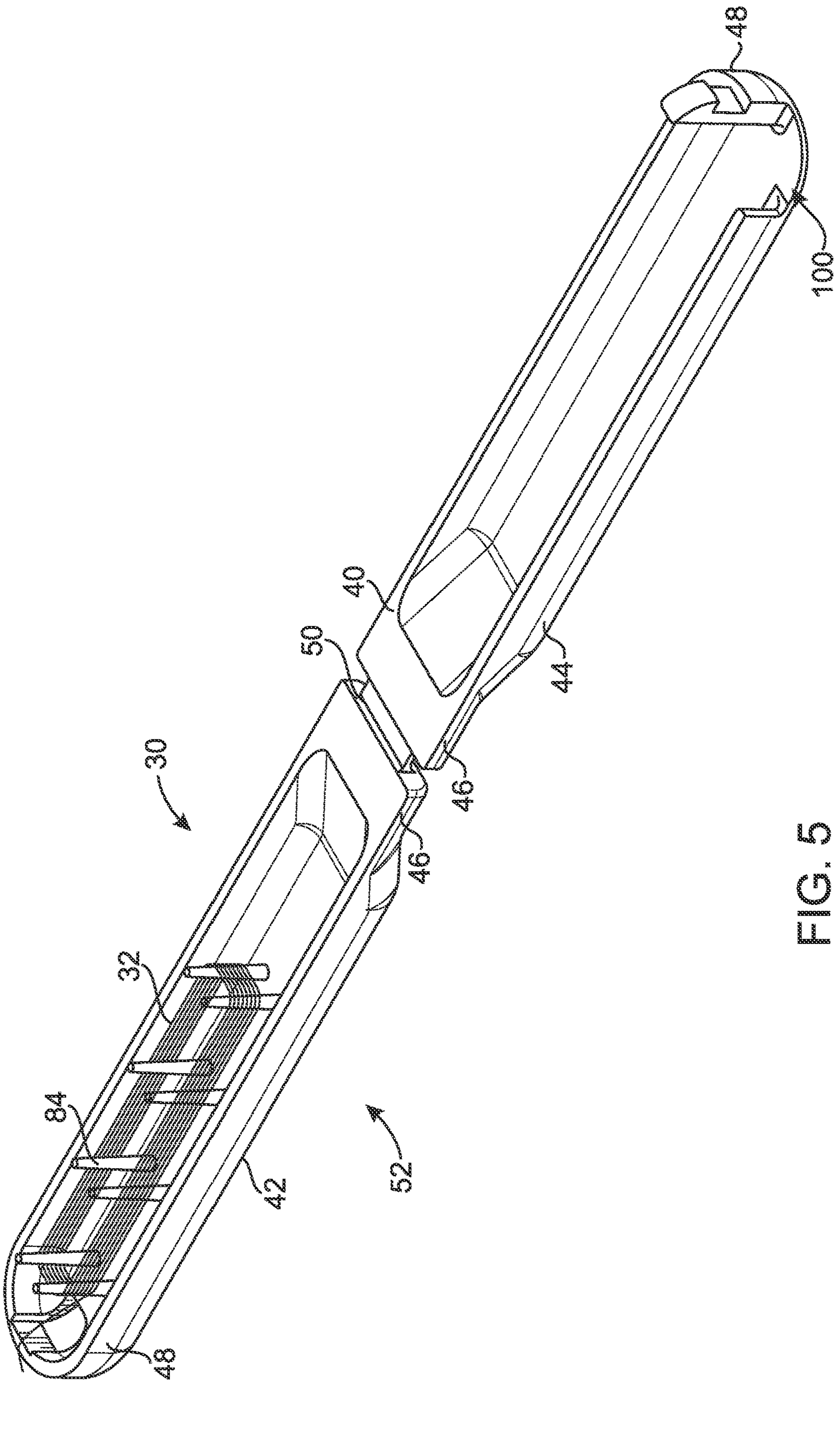
FIG. 5 is a top perspective view of the clamshell body in the open position and having a suture would around a suture retainer.
Figure 6:
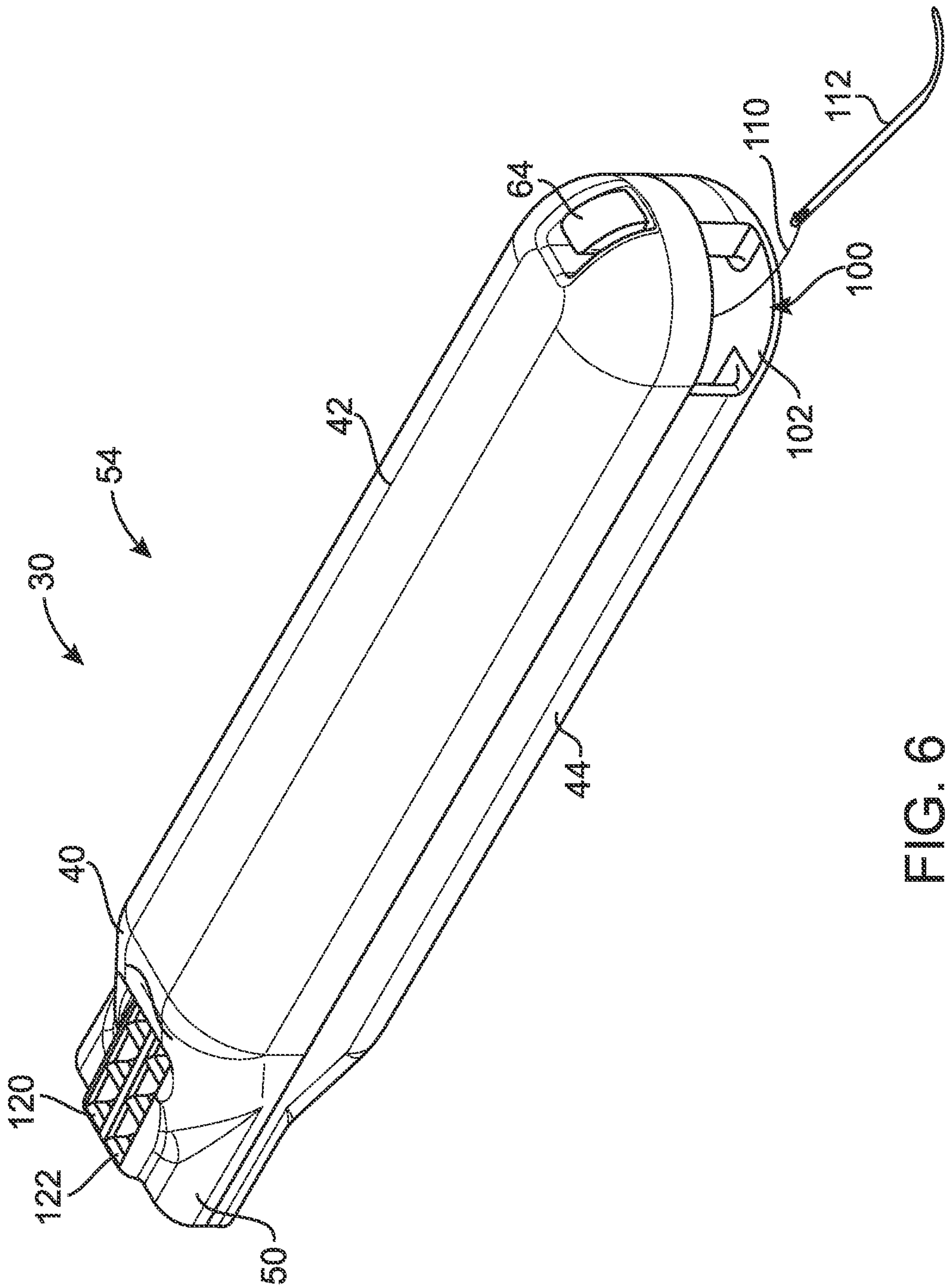
FIG. 6 is a top perspective view of the clamshell body in the closed position and having an end of the suture extending through an opening.

FIG. 5 illustrates the suture 32 wound around the suture retainer 80. The suture 32 is would around the outside of the suture retainer 80 in loops. That is, the suture 32 is wound around the outside of each of the plurality of pegs 84. As illustrated in FIG. 6, in the closed position 54, the end 110 of the suture 32 extends through the opening 100. Accordingly, the needle 112 can be pulled by the fingers 14 of the robotic arm 12 to unwind the suture 32 and pull the suture 32 through the opening 100 during the surgical procedure. By unwinding the suture 32, the suture may be passed through the patient's tissue to facilitate closing the surgical site.

Figure 7:
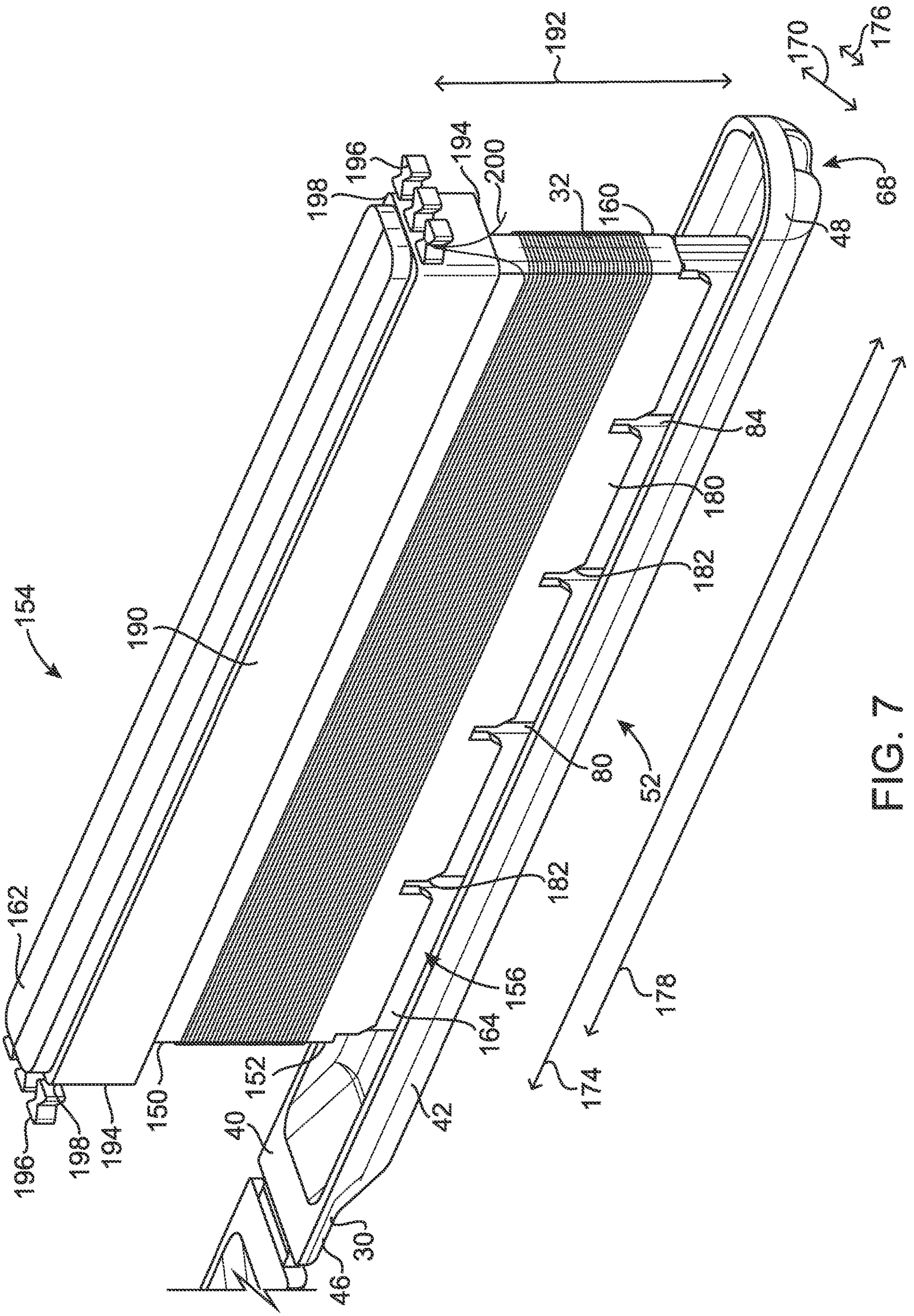
FIG. 7 is a perspective view of an embodiment of a cartridge configured to receive the suture.

Referring now to FIG. 7, a cartridge 150 for positioning the suture 32 in the device 30 includes a body 152. The body 152 includes a top end 154 and a bottom end 156. A main body 160 extends from a flange 162 at the top end 154 to a lower body 164 at the bottom end 156. The main body 160 has a width 170 and a length 174 that is larger than a width 176 and a length 178 of the lower body 164 so that a ledge 180 is formed between the main body 160 and the lower body 164. A plurality of notches 182 are formed at the ledge 180 and extend into the main body 160.

A sliding bracket 190 extends around the main body 160. The bracket 190 is configured to slide along a height 192 of the main body 160. The bracket 190 is prevented from sliding off the top end 154 of the cartridge 150 by the flange 162. The bracket 190 includes opposite ends 194 that each have a plurality of suture tabs 196 attached thereto. The suture tabs 196 each include a break point 198 that enables the tab 196 to be detached from the bracket 190.

During the surgical procedure, the suture 32 is wound around the main body 160 by a caregiver. In some embodiments, the suture 32 is pre-loaded around the main body 160 prior to the surgical procedure. An end 200 of the suture 32 positioned opposite the end 110 of the suture 32 is secured to one of the suture tabs 196. In some embodiments, the suture 32 may be utilized without the suture tab 196.

The lower body 164 of the cartridge 150 is removably positioned in the suture retainer 80. In the illustrative embodiment, the lower body 164 is positioned between the pegs 84. Each peg 84 extends into one of the notches 182 in the main body 160 to secure the cartridge 150 into the device 30. With the cartridge 150 positioned in the device 30, the bracket 190 is slid down the main body 160 to push the suture 32 off of the main body 160 and around the suture retainer 80, e.g. around the pegs 84.

With the suture 32 secured around the suture retainer 80, the suture tab 196 to which the end 200 of the suture 32 is secured is broken off of the bracket 190 at the break point 198. In some embodiments, the suture tab 196 is broken off the bracket 190 prior to sliding the suture 32 onto the suture retainer 80. The cartridge 150 is then removed from the device 30 and the device 30 is moved to the closed position, shown in FIG. 6, with the end 110 of the suture 32 extending through the opening 100. The device is inserted into the surgical site of the patient and the suture 32 is pulled from the device 30 to stitch the surgical site. When all of the suture 32 is removed from the device 30, the suture tab 196 anchors against the tissue of the patient inside the surgical site to secure the suture 32.

Figure 8:
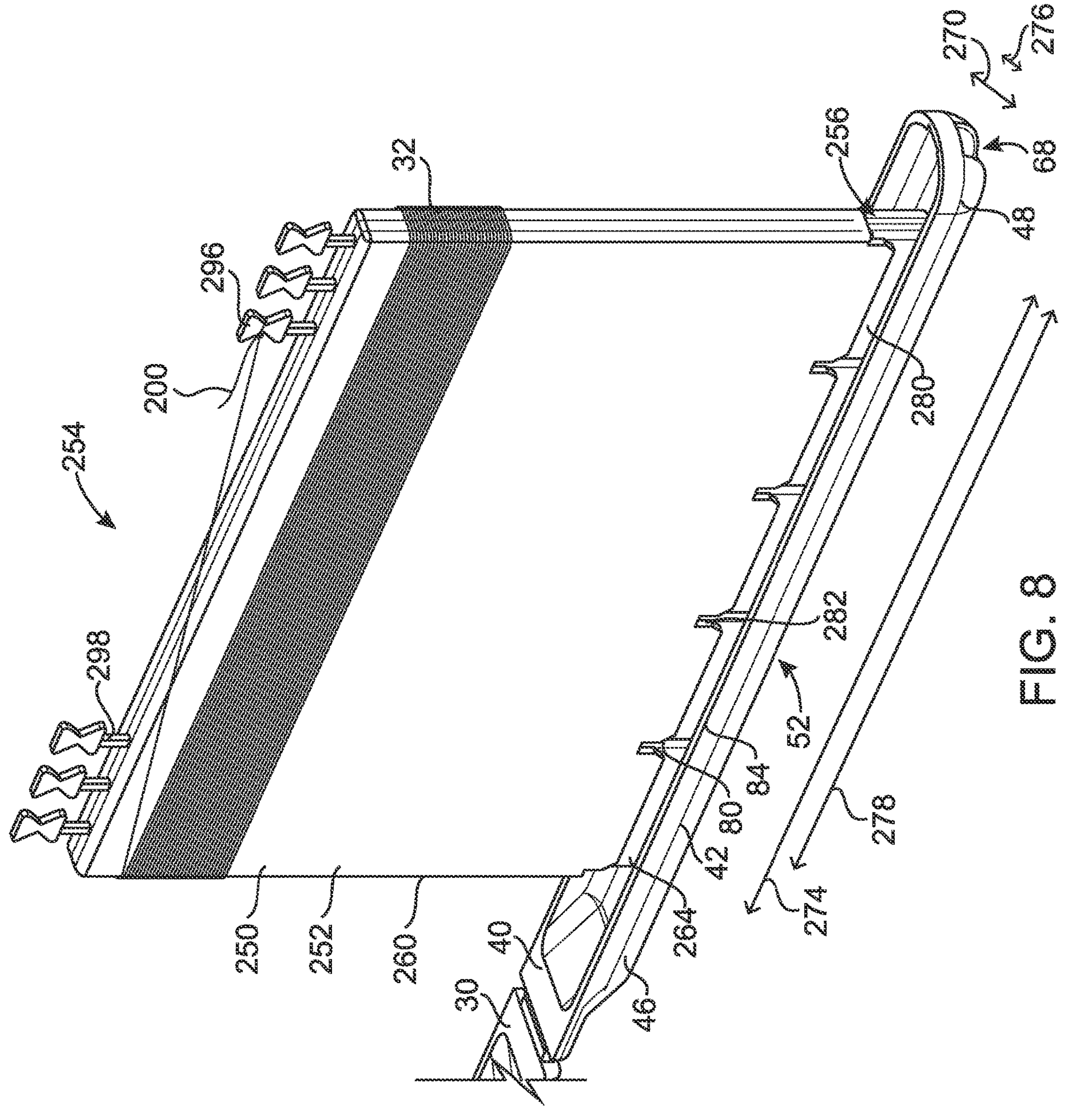
FIG. 8 is a perspective view of another embodiment of a cartridge configured to receive the suture.

Referring now to FIG. 8, another cartridge 250 for positioning the suture 32 in the device 30 includes a body 252. The body 252 includes a top end 254 and a bottom end 256. A main body 260 extends from the top end 254 to a lower body 264 at the bottom end 256. The main body 260 has a width 270 and a length 274 that is larger than a width 276 and a length 278 of the lower body 264 so that a ledge 280 is formed between the main body 260 and the lower body 264. A plurality of notches 282 are formed at the ledge 280 and extend into the main body 260. The main body 260 includes a plurality of suture tabs 296 extending from the top end 254. The suture tabs 296 each include a break point 298 that enables the tab 296 to be detached from the main body 260. In some embodiments, the cartridge 250 may also include a sliding bracket similar to sliding bracket 190.

During the surgical procedure, the suture 32 is wound around the main body 260 by a caregiver. In some embodiments, the suture 32 is pre-loaded around the main body 260 prior to the surgical procedure. The end 200 of the suture 32 is secured to one of the suture tabs 296. In some embodiments, the suture 32 may be utilized without the suture tab 296.

The lower body 264 of the cartridge 250 is removably positioned in the suture retainer 80. In the illustrative embodiment, the lower body 264 is positioned between the pegs 84. Each peg 84 extends into one of the notches 282 in the main body 160 to secure the cartridge 250 into the device 30. With the cartridge 250 positioned in the device 30, a caregiver slides the suture 32 down the main body 260 to push the suture 32 off of the main body 260 and around the suture retainer 80, e.g. around the pegs 84. In some embodiments, a sliding bracket similar to sliding bracket 190 is used to move the suture 32 onto the suture retainer 80.

With the suture 32 secured around the suture retainer 80, the suture tab 296 to which the end 200 of the suture 32 is secured is broken off of the bracket 290 at the break point 298. In some embodiments, the suture tab 296 is broken off prior to moving the suture 32 onto the suture retainer 80. The cartridge 250 is then removed from the device 30 and the device 30 is moved to the closed position, shown in FIG. 6, with the end 110 of the suture 32 extending through the opening 100. The device is inserted into the surgical site of the patient and the suture 32 is pulled from the device 30 to stitch the surgical site. When all of the suture 32 is removed from the device 30, the suture tab 296 anchors against the tissue of the patient inside the surgical site to secure the suture 32.

Figure 9:
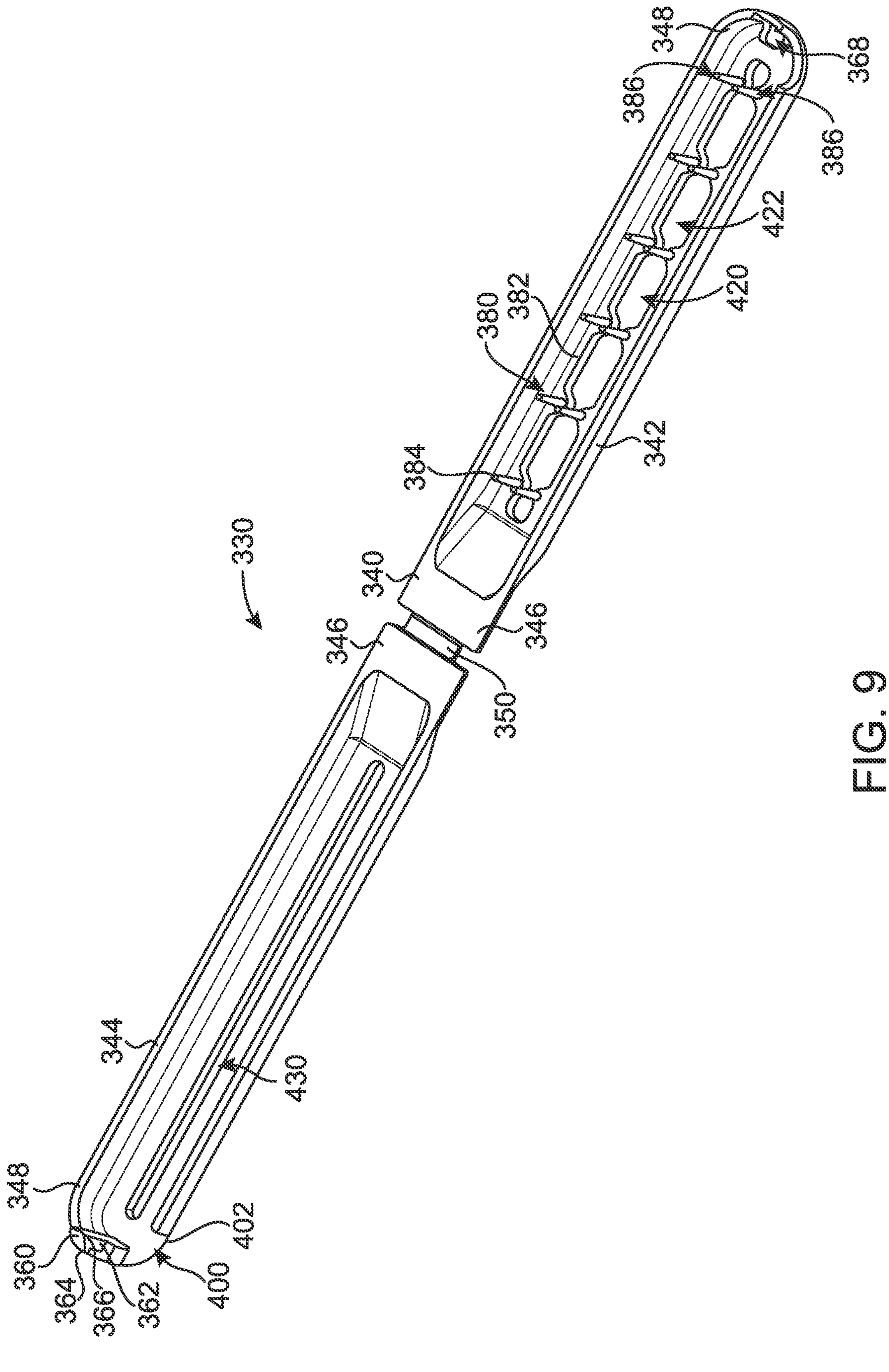
FIG. 9 is a top perspective view of another suturing device having a clamshell body including a first side coupled to a second side by a hinge at a hinge end, wherein the clamshell body is in an open position.

Referring now to FIG. 9, a suturing device 330 is configured for use with the system 10 by securing the suturing device 330 to one of the plurality of fingers 14 of the robotic arm 12. The suturing device 330 is configured to be inserted into a surgical site of a patient to facilitate closing the surgical site after a surgical procedure. The suturing device 330 retains a suture that can be pulled from the suturing device 330 to facilitate closing the surgical site. The suture is configured to be pulled from the suturing device 330 while the suturing device 330 is inserted in the surgical site, e.g. inside the patient. The suture is threaded through tissue that is to be closed before the suturing device 330 is removed from the surgical site. After the suturing device 330 is removed from the surgical site the suture is tied together in at least one location to close the surgical site. In at least one embodiment, the suture is wound within the suturing device 330 by a caregiver or technician prior to the surgical procedure. Accordingly, the suturing device 330 can accommodate any suture type used within a healthcare facility. A caregiver or technician selects the appropriate suture type for the surgical procedure, and the appropriate suture type is wound within the suturing device 330 at the healthcare facility prior to the surgical procedure. In another embodiment, the suturing device 330 may be pre-loaded with the suture.

The suturing device 330 includes a clamshell body 340 having a first side 342 and a second side 344. Each of the first side 342 and the second side 344 includes a hinge end 346 and a cantilevered end 348. A pair of sidewalls 356 extend between the hinge end 346 and the cantilevered end 348 of each of the first side 342 and the second side 344. The first side 342 is coupled to the second side 344 by a hinge 350 at the hinge end 346 of the first side 342 and the second side 344. The hinge 350 enables the clamshell body 340 to articulate between an open position and a closed position. The cantilevered end 348 of the second side 344 of the clamshell body 340 includes latch 360 having an arm 362 and an outwardly extending flange 364 extending from an end 366 of the arm 362. The cantilevered end 348 of the first side 342 of the clamshell body 340 includes an opening 368. The latch 360 is configured to extend though the opening 368 so that the flange 364 secures the first side 342 of the clamshell body 340 to the second side 344 of the clamshell body 340 when the clamshell body 340 is in the closed position.

A suture retainer 380 is positioned within the clamshell body 340 and configured to receive the suture. The suture retainer 380 extends from an inner wall 382 of the first side 342 of the clamshell body 340. The suture retainer 380 includes a plurality of pegs 384 extending from the inner wall 382. In the illustrative embodiment, the plurality of pegs 384 are arranged in two rows 386 extending between the hinge end 346 and the cantilevered end 348 of the first side 342 of the clamshell body 340. In some embodiments, the caregiver or technician winds the suture around the suture retainer 380 at the healthcare facility. In other embodiments, the suture is pre-loaded around the suture retainer 380.

An opening 400 is formed in the cantilevered end 348 of the second side 344 of the clamshell body 340. In the illustrative embodiment, the opening 400 is formed in a corner 402 of the cantilevered end 348 of the second side 344 of the clamshell body 340. In other embodiments, the opening 400 may be centered in the cantilevered end 348 of the second side 344 of the clamshell body 340. In yet another embodiment, the opening 400 may be formed in the sidewall 356 of the second side 344. It may also be contemplated that the opening 400 is formed in a sidewall 356 of the first side 342, in some embodiments. When the suture is wound around the suture retainer 380, and end of the suture having a needle extends from the suturing device 330.

A first side slot 420 extends through the first side 342 of the clamshell body 340. The suture retainer 380 extends around the first side slot 420. That is, the plurality of pegs 384 is arranged around the first side slot 420. The first side slot 420 includes a plurality of notches 422. Each peg 384 is positioned between a pair of adjacent notches 422. A second side slot 430 extends through the second side 344 of the clamshell body 340. When the clamshell body 340 is positioned in the closed position, the first side slot 420 is aligned with the second side slot 430.

Figure 10:
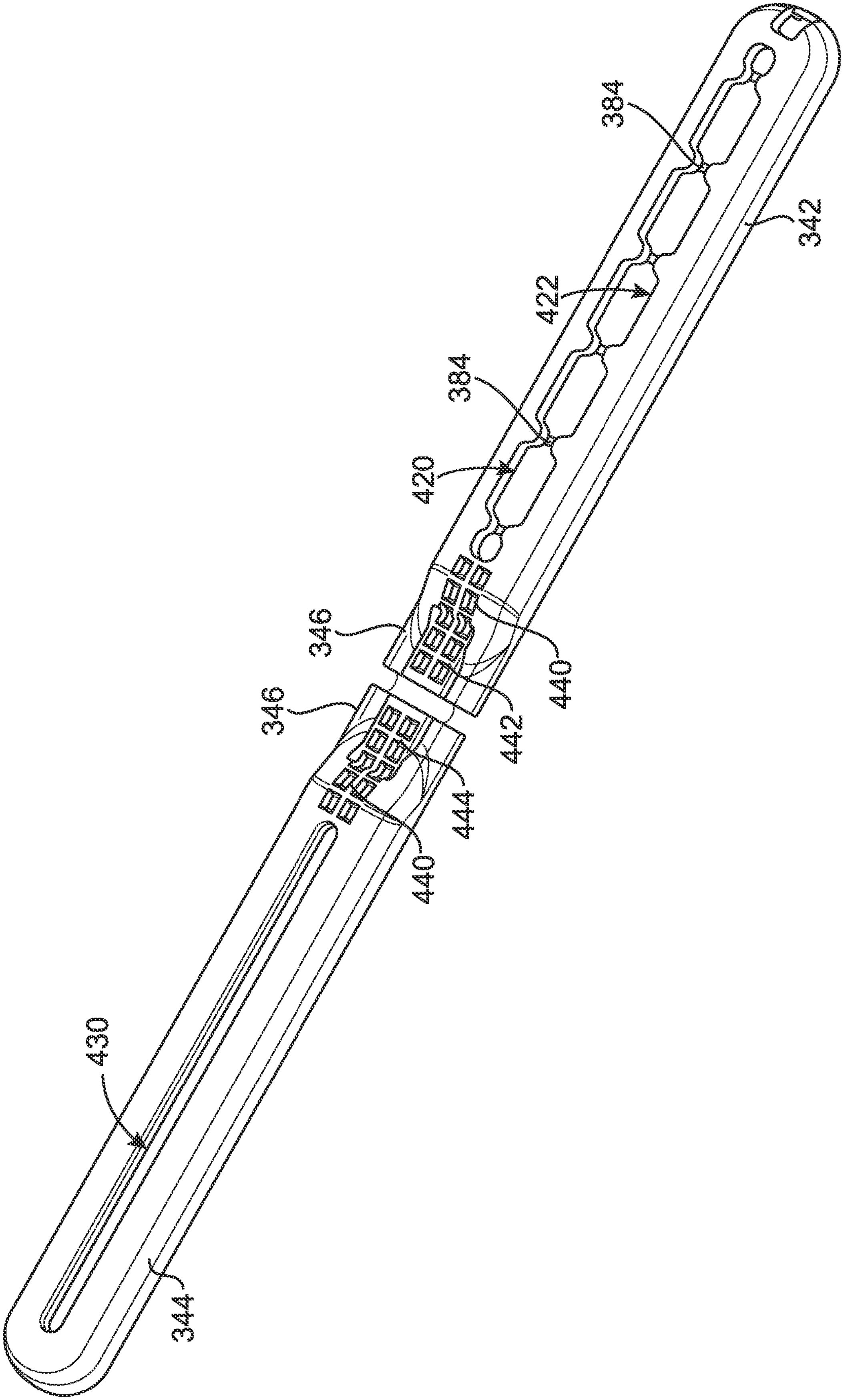
FIG. 10 is a bottom perspective view of the clamshell body shown in FIG. 9 in the open position.

Referring now to FIG. 10, notches 440 are formed adjacent the hinge end 346 of each of the first side 342 and the second side 344 of the suturing device 330. In particular, a first set of notches 442 are formed adjacent the hinge end 346 of the first side 342, and a second set of notches 444 are formed adjacent the hinge end 346 of the second side 344. In the closed position, the first set of notches 442 are positioned opposite the second set of notches 444. The fingers 14 of the robotic arm 12 are configured to grip the suturing device 330 at the notches 440 so that the suturing device 330 is secured to the system 10 during the surgical procedure.

Figure 11:
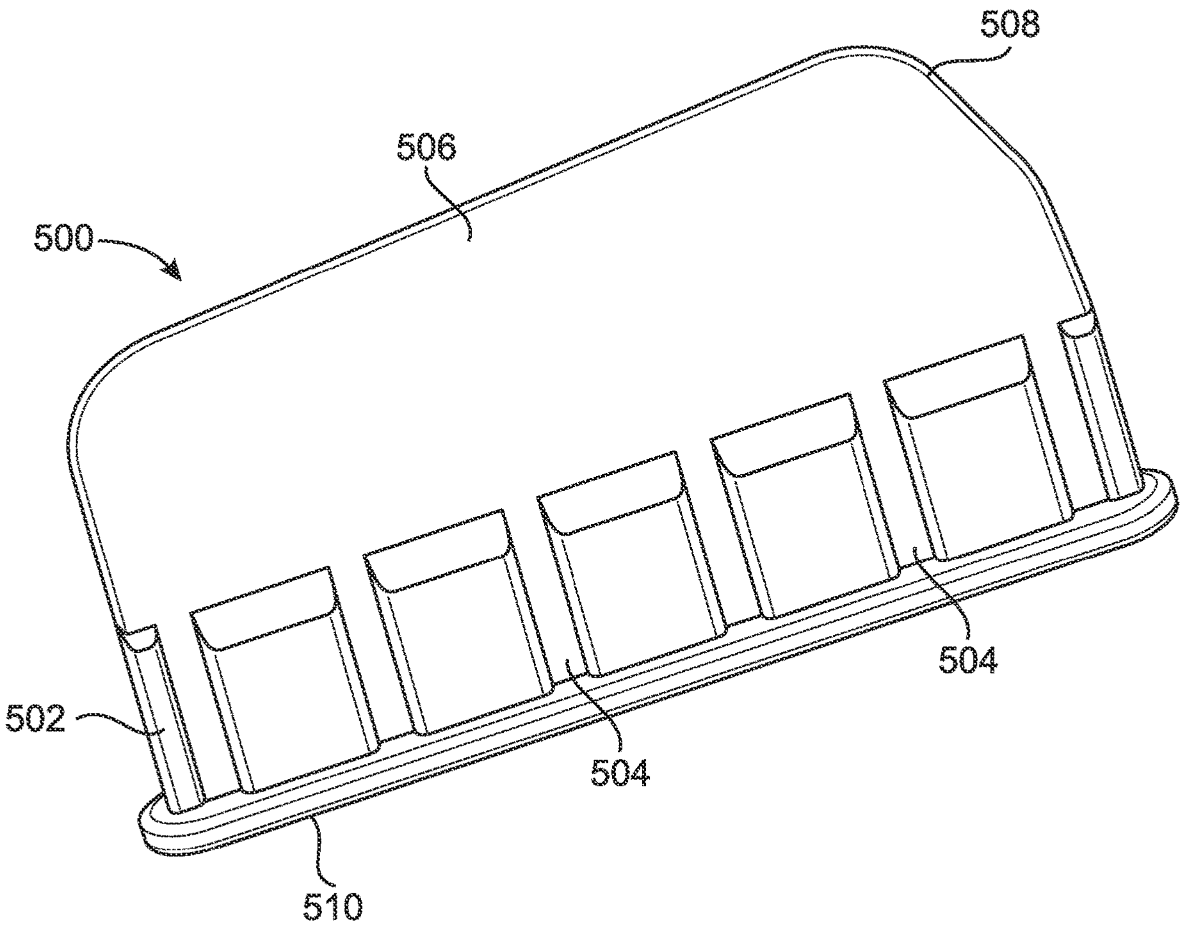
FIG. 11 is a perspective view of another embodiment of a cartridge configured to receive the suture.
Figure 12:
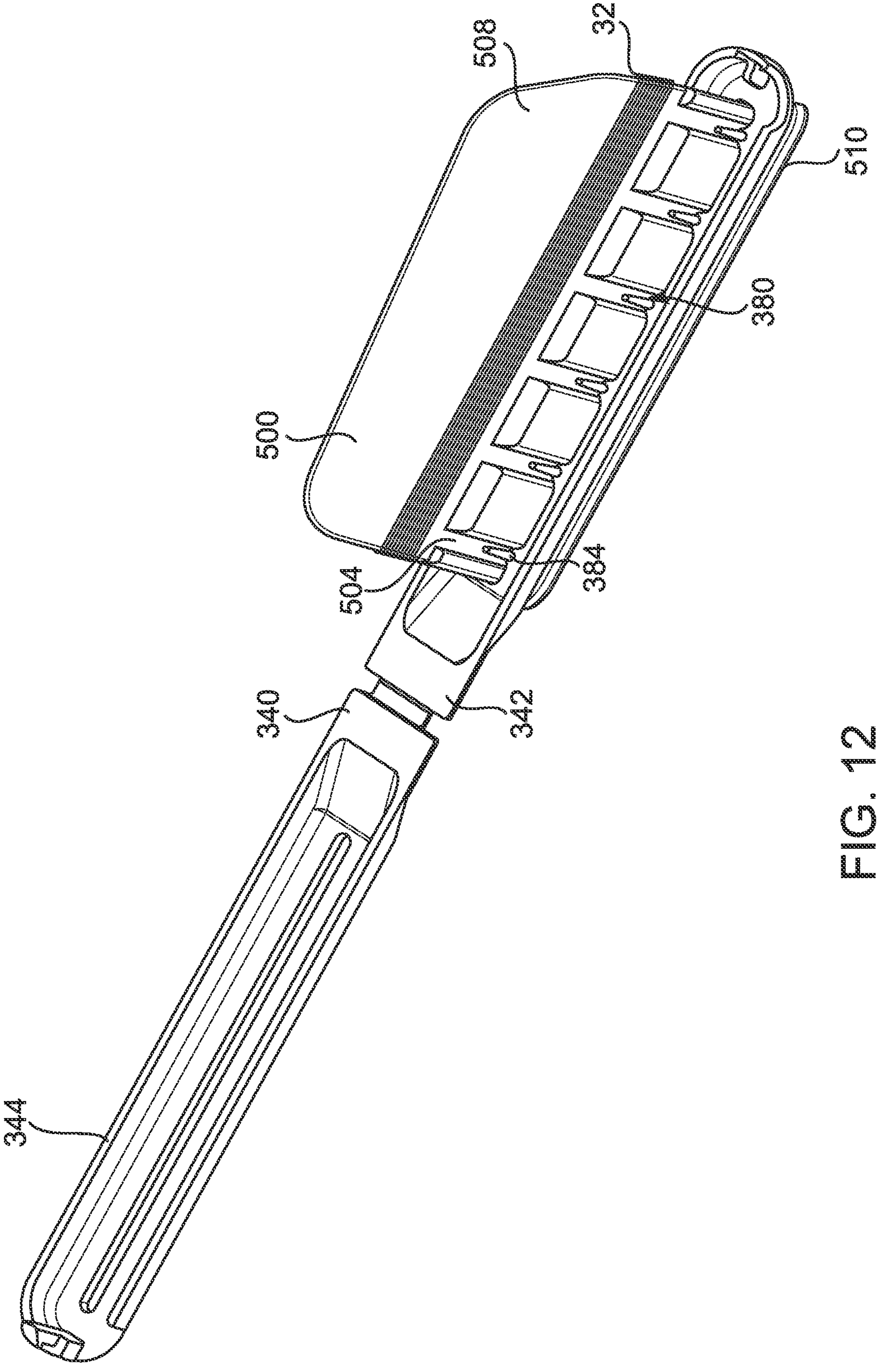
FIG. 12 is a perspective view of the cartridge shown in FIG. 11 inserted into the first side of the clamshell body shown in FIG. 9, wherein the clamshell body is in the open position.
Figure 13:
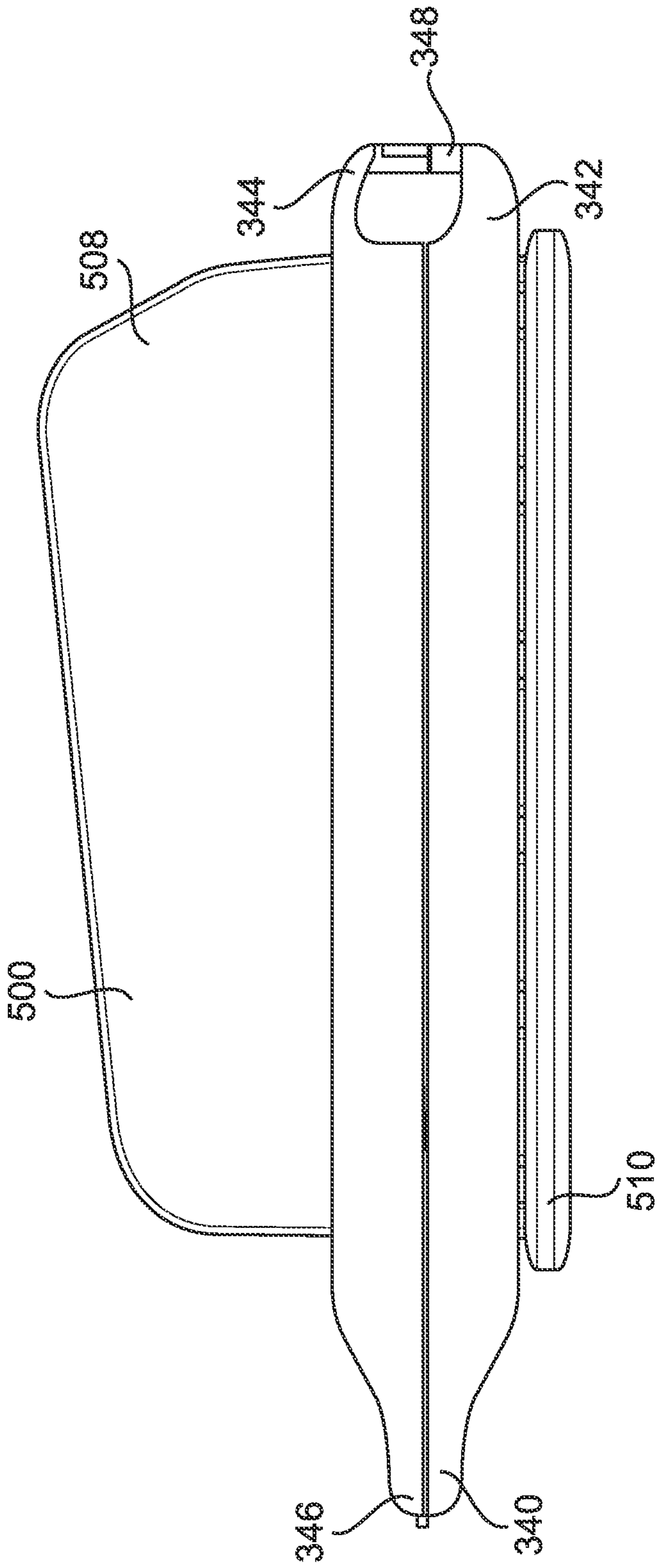
FIG. 13 is a perspective view of the cartridge shown in FIG. 11 inserted into the first side and the second side of the clamshell body shown in FIG. 9, wherein the clamshell body is in the closed position.

Referring to FIG. 11, a cartridge 500 is configured to be removably inserted through the first side slot 420. The suture is configured to be wound around the cartridge 500 to assist in positioning the suture around the suture retainer 380. The cartridge 500 includes a lower body 502 having a plurality of notches 504 formed on each side of the cartridge 500. Each of the plurality of pegs 384 is configured to rest within one of the plurality of notches 504 when the cartridge 500 is inserted through the first side slot 420, as illustrated in FIG. 12. At least a portion of the cartridge 500 is configured to extend through the second side slot 430 when the cartridge 500 is inserted through the first side slot 420 and the clamshell body 340 is moved to the closed position, as illustrated in FIG. 13. The cartridge 500 also includes a top 506 having a sloped end 508 to enable the at least a portion of the cartridge 500 to move through the second side slot 430 when the clamshell body 340 is moved to the closed position. A base 510 of the cartridge 500 is sized greater than the lower body 502 to prevent the entire cartridge 500 from passing through the first side slot 420.

Figure 14:
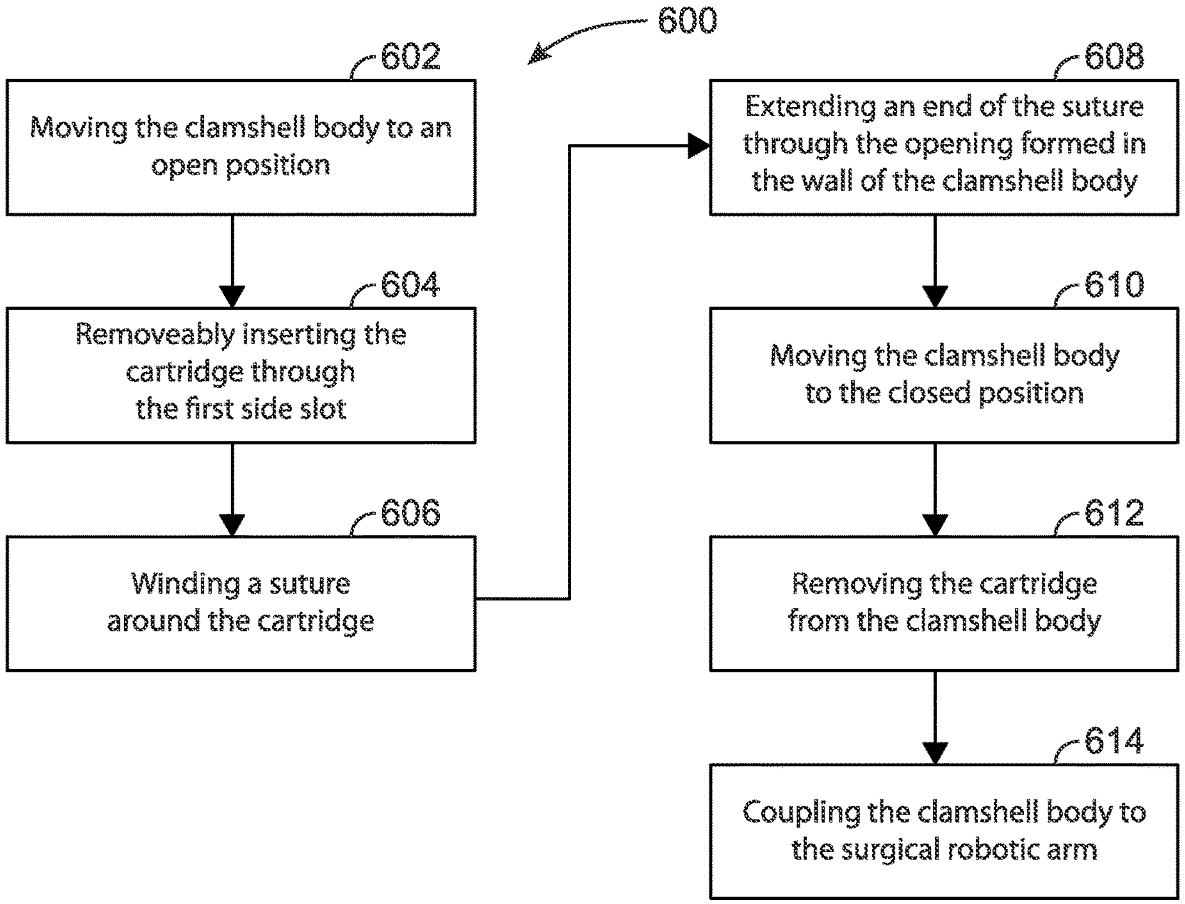
FIG. 14 is a flowchart of a method of preparing the suturing device shown in FIG. 9.

Referring now to FIG. 14, a method 600 of preparing the suturing device 330 including the clamshell body 340 includes moving the clamshell body 340 to an open position wherein the first side 342 of the clamshell body 340 is rotated away from the second side 344 of the clamshell body 340, at block 602. At block 604, the cartridge 500 is removably inserted through the first side slot 420 in the first side of 342 the clamshell body 340. The cartridge 500 extends through the suture retainer 380 when the cartridge 500 is inserted into the first side slot 420. That is, the cartridge 500 is inserted between the plurality of pegs 384 when the cartridge 500 is inserted into the first side slot 420. Each of the plurality of pegs 384 is positioned to rest within one of the plurality of notches 504 when the cartridge 500 is inserted through the first side slot 420. At block 606, a suture is wound around the cartridge 500 to assist in positioning the suture around a suture retainer 380 positioned within the clamshell body 340. At block 608, an end of the suture is extended through the opening 400 formed in the wall of the clamshell body 340.

At block 610 the clamshell body 340 is moved to the closed position wherein the first side 342 of the clamshell body 340 is rotated toward the second side 344 of the clamshell body 340. At least a portion of the cartridge 500 extends through the second side slot 430 extending through the second side 344 of the clamshell body 340 when the cartridge 500 is inserted through the first side slot 420 and the clamshell body 340 is moved to the closed position. The at least a portion of the cartridge 500 is guided through the second side slot 430 by the sloped end 508 of the cartridge 500 when the clamshell body 340 is moved to the closed position. The clamshell body 340 is moved to the closed position to assist in positioning the suture around the suture retainer 380 when the cartridge 500 is inserted through the first side slot 420. That is, when moving the clamshell body 340 to the closed position, the second side 344 of the clamshell body 340 pushes the suture down the cartridge 500 and onto the suture retainer 380. The end of the suture extends through the opening 400 when the clamshell body 340 is in the closed position so that the suture is accessible within the surgical site of the patient.

At block 612, the cartridge 500 is removed from the clamshell body 340 through the first side slot 420 after the cartridge 500 is inserted through the first side slot 420 and the clamshell body 340 is moved to the closed position. It should be noted that the suture may be positioned on the suture retainer 380 during the medical procedure for the patient or before a medical procedure for the patient. The method 600 may also include coupling the clamshell body 340 to the surgical robotic arm 12 after securing the suture within the suturing device 330, at block 614.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless cannot be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and many combinations of aspects and principles are possible in light of the various embodiments provided above.

The invention claimed is:

1. A method of preparing a suturing device including a clamshell body configured to be inserted into a surgical site of a patient, the method comprising:

moving the clamshell body to an open position wherein a first side of the clamshell body is rotated away from a second side of the clamshell body, wherein the first side is coupled to the second side by a hinge at a hinge end;

removeably inserting a cartridge through a first side slot extending through the first side of the clamshell body;

winding a suture around the cartridge to assist in positioning the suture around a suture retainer positioned within the clamshell body;

extending an end of the suture through an opening formed in a wall of the clamshell body; and moving the clamshell body to a closed position wherein the first side of the clamshell body is rotated toward the second side of the clamshell body, wherein the end of the suture is configured to extend through the opening when the clamshell body is in the closed position so that the suture is accessible within the surgical site of the patient.

2. The method of claim 1, further comprising inserting the cartridge through the suture retainer when the cartridge is inserted into the first side slot.

3. The method of claim 2, wherein: the suture retainer includes a plurality of pegs arranged around the first side slot, and the method further comprises inserting the cartridge between the plurality of pegs when the cartridge is inserted into the first side slot.

4. The method of claim 3, wherein: the cartridge includes a plurality of notches, and the method further comprises positioning each of the plurality of pegs within one of the plurality of notches when the cartridge is inserted through the first side slot.

5. The method of claim 1, further comprising extending at least a portion of the cartridge through a second side slot extending through the second side of the clamshell body when the cartridge is inserted through the first side slot and the clamshell body is moved to the closed position.

6. The method of claim 5, further comprising moving the clamshell body to the closed position to assist in positioning the suture around the suture retainer when the cartridge is inserted through the first side slot.

7. The method of claim 6, further comprising removing the cartridge from the clamshell body through the first side slot after the cartridge is inserted through the first side slot and the clamshell body is moved to the closed position.

8. The method of claim 5, wherein: the cartridge includes a sloped end, and the method further comprises guiding the at least a portion of the cartridge to move through the second side slot with the sloped end when the clamshell body is moved to the closed position.

9. The method of claim 1, further comprising positioning the suture on the suture retainer at least one of during a medical procedure for the patient and before a medical procedure for the patient.

10. The method of claim 1, further comprising coupling the clamshell body to a surgical robotic arm.

11. A method of preparing a suturing device including a body, the method comprising:

moving the body to an open position;

removeably inserting a cartridge into a suture retainer positioned within the body;

utilizing the cartridge to assist in positioning a suture around the suture retainer; and moving the body to a closed position, wherein an end of the suture is configured to extend through an opening in the body when the body is in the closed position.

12. The method of claim 11, further comprising inserting the cartridge through the suture retainer when the cartridge is inserted into a first side slot in the body.

13. The method of claim 12, wherein: the suture retainer includes a plurality of pegs arranged around the first side slot, and the method further comprises inserting the cartridge between the plurality of pegs when the cartridge is inserted into the first side slot.

14. The method of claim 13, wherein: the cartridge includes a plurality of notches, and the method further comprises positioning each of the plurality of pegs within one of the plurality of notches when the cartridge is inserted through the first side slot.

15. The method of claim 11, further comprising extending at least a portion of the cartridge through a second side slot extending through the body when the cartridge is inserted through the first side slot and the body is moved to the closed position.

16. The method of claim 15, further comprising moving the body to the closed position to assist in positioning the suture around the suture retainer when the cartridge is inserted through the first side slot.

17. The method of claim 16, further comprising removing the cartridge from the body through the first side slot after the cartridge is inserted through the first side slot and the body is moved to the closed position.

18. The method of claim 15, wherein: the cartridge includes a sloped end, and the method further comprises guiding the at least a portion of the cartridge to move through the second side slot with the sloped end when the body is moved to the closed position.

19. The method of claim 11, further comprising positioning the suture on the suture retainer at least one of during a medical procedure for the patient and before a medical procedure for the patient.

20. The method of claim 11, further comprising coupling the body to a surgical robotic arm.

* * * * *